(12) United States Patent
Sofer et al.

(10) Patent No.: US 10,605,745 B2
(45) Date of Patent: Mar. 31, 2020

(54) GUIDED INSPECTION OF A SEMICONDUCTOR WAFER BASED ON SYSTEMATIC DEFECTS

(71) Applicant: Applied Materials Israel Ltd., Rehovot (IL)

(72) Inventors: Yotam Sofer, Givataim (IL); Boaz Cohen, Lehavim (IL); Saar Shabtay, Moshav Mishmeret (IL); Eli Buchman, Rehovot (IL)

(73) Assignee: APPLIED MATERIALS ISRAEL LTD., Rehovot (IL)

(*) Notice: Subject to any disclaimer, the term of this patent is extended or adjusted under 35 U.S.C. 154(b) by 0 days.

(21) Appl. No.: 16/022,566

(22) Filed: Jun. 28, 2018

(65) Prior Publication Data
US 2020/0003700 A1   Jan. 2, 2020

(51) Int. Cl.
G01N 21/95   (2006.01)
G01N 21/956   (2006.01)

(52) U.S. Cl.
CPC ....... *G01N 21/9501* (2013.01); *G01N 21/956* (2013.01)

(58) Field of Classification Search
CPC .................. G01N 21/9501; G01N 21/956
USPC ............... 356/239.1–239.8, 237.1–237.6
See application file for complete search history.

(56) References Cited

U.S. PATENT DOCUMENTS

2011/0276935  A1*  11/2011  Fouquet ............... G06T 7/0006
                                                      716/112

* cited by examiner

*Primary Examiner* — Tri T Ton
(74) *Attorney, Agent, or Firm* — Lowenstein Sandler LLP

(57) ABSTRACT

A candidate defect may be identified at a semiconductor wafer. A determination may be made as to whether the candidate defect at the semiconductor wafer corresponds to a systematic defect or a random defect. In response to determining that the candidate defect at the semiconductor wafer corresponds to a systematic detect, the candidate defect at the semiconductor wafer may be provided to a defect review tool for review by the defect review tool.

17 Claims, 5 Drawing Sheets

GUIDED INSPECTION OF A SEMICONDUCTOR WAFER BASED ON SYSTEMATIC DEFECTS

TECHNICAL FIELD

The present disclosure generally relates to guided inspection, and more specifically, relates to guided inspection of a semiconductor wafer based on systematic defects.

BACKGROUND

Fabrication of a semiconductor device may utilize submicron features associated with ultra large scale integration. Such fabrication processes may require a formation of semiconductor device features with high precision and uniformity which may necessitate careful monitoring of the fabrication process. For example, frequent and detailed inspection of a semiconductor wafer may be performed to detect defects of the semiconductor wafer. The detailed inspection may correspond to an analysis of an inspection image of the semiconductor wafer.

SUMMARY

The following is a simplified summary of the disclosure in order to provide a basic understanding of some aspects of the disclosure. This summary is not an extensive overview of the disclosure. It is intended to neither identify key or critical elements of the disclosure, nor delineate any scope of the particular implementations of the disclosure or any scope of the claims. Its sole purpose is to present some concepts of the disclosure in a simplified form as a prelude to the more detailed description that is presented later.

Implementations of the disclosure may correspond to a system that includes a memory and a processing device to identify a candidate defect at a semiconductor wafer and determine whether the candidate defect at the semiconductor wafer corresponds to a systematic defect or a random defect. In response to determining that the candidate defect at the semiconductor wafer corresponds to a systematic detect, the processing device may provide the candidate defect at the semiconductor wafer to a defect review tool for review by the defect review tool.

In some implementations, to determine whether the candidate defect at the semiconductor wafer corresponds to a systematic defect or a random defect, the processing device may further to identify a pattern associated with the candidate defect and identify other candidate defects at the semiconductor wafer that are associated with the same pattern. Furthermore, the processing device may generate a combined defect probability score for the candidate defect based on a defect probability score of the candidate defect and other defect probability scores of the other candidate defects that are associated with the same pattern.

In some implementations, the pattern associated with the candidate defect may correspond to a structure of the semiconductor wafer that is at or approximate to the candidate defect and the other candidate defects that are associated with the same pattern may correspond to candidate defects that are at or approximate another structure of the semiconductor wafer with the same pattern.

In some implementations, the processing device may determine that the candidate defect is a systematic defect when the combined defect probability score for the candidate defect satisfies a threshold value and the processing device may further determine that the candidate defect is a random defect when the combined defect probability score for the candidate defect does not satisfy the threshold value.

In some implementations, the combined defect probability score is higher when a number of the other candidate defects that are associated with the same pattern as the candidate defect is larger than when a number of the other candidate defects that are associated with the same pattern as the candidate defect is smaller.

In some implementations, the candidate defect is identified based on an optical image of the semiconductor wafer and the candidate defect is determined to corresponds to a systematic defect or a random defect based on design data of the semiconductor wafer.

In some implementations, the processing device may further determine to not provide the candidate defect at the semiconductor wafer to the defect review tool for review by the defect review tool in response to determining that the candidate defect at the semiconductor wafer corresponds to a random detect.

In some implementations a method may identify a candidate defect at a semiconductor wafer, determine, by a processing device, whether the candidate defect at the semiconductor wafer corresponds to a systematic defect or a random defect, and in response to determining that the candidate defect at the semiconductor wafer corresponds to a systematic detect, provide the candidate defect at the semiconductor wafer to a defect review tool for review by the defect review tool.

In some implementations, a non-transitory computer readable medium may include instructions which when executed by a processing device cause the processing device to may identify a candidate defect at a semiconductor wafer, determine whether the candidate defect at the semiconductor wafer corresponds to a systematic defect or a random defect, and in response to determining that the candidate defect at the semiconductor wafer corresponds to a systematic detect, provide the candidate defect at the semiconductor wafer to a defect review tool for review by the defect review tool.

BRIEF DESCRIPTION OF THE DRAWINGS

The present disclosure will be understood more fully from the detailed description given below and from the accompanying drawings of various implementations of the disclosure.

DETAILED DESCRIPTION

Figure 1:
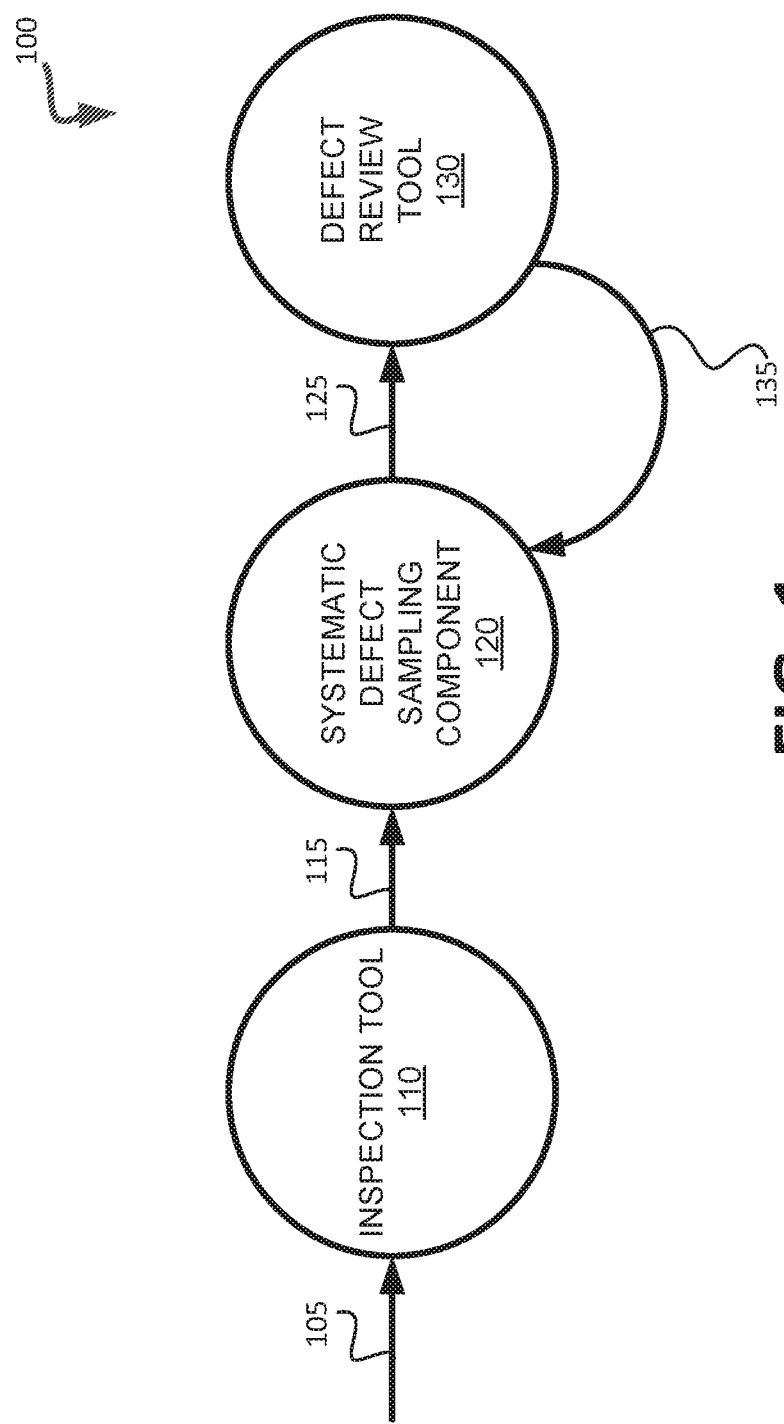
FIG. 1 illustrates an example environment of a guided inspection system in accordance with some embodiments of the present disclosure.

Aspects of the present disclosure are directed to guided inspection of a semiconductor wafer based on systematic defects. In general, a semiconductor wafer inspection system may be used to perform an examination of a semiconductor wafer. For example, the semiconductor wafer inspection system may be used to identify defects at the semiconductor wafer.

The semiconductor wafer inspection system may include an optical tool and a defect review tool. For example, the optical tool may be used to identify potential or candidate defects at a semiconductor wafer after or during a fabrication process. Subsequently, the defect review tool may be used to review, classify, or determine whether the candidate defects are actual defects or are not defects (e.g., a 'false alarm'). In circumstances where the design or other such technology (e.g., fabrication process, use of materials, or design features) of the semiconductor wafer is newer, the fabrication process of the semiconductor wafer may be unstable and result in a lower yield for the fabrication of the semiconductor wafer. If the design being implemented in the semiconductor wafer is flawed, then the fabrication process may also result in multiple defects at the semiconductor wafer.

Aspects of the present disclosure address the above and other deficiencies by guiding an inspection of a semiconductor wafer based on systematic defects. For example, the inspection of a semiconductor wafer may be based on identifying potential defects that are systematic defects by providing a systematic defect to be reviewed by a defect review tool. The potential defect may be identified as a systematic defect by using a combination of a defect score (e.g., a probability of a potential defect being an actual defect based on an optical image of the potential defect) and a pattern corresponding to the location of the potential defect (e.g., computer aided design (CAD) data specifying a pattern or a structure of a circuit design being implemented at the semiconductor wafer). For example, a potential defect may be identified based on an optical image of the semiconductor wafer and a pattern associated with the potential defect may be identified. The pattern may be a structure or a part of a structure implemented in the semiconductor wafer that is at or approximate to the potential defect. Other potential defects with the same or similar patterns may also be identified. Furthermore, a defect score for each of the potential defect and the other potential defects may be received. The defect scores may indicate a probability that the corresponding potential defect may be an actual defect. For example, the defect score for a particular potential defect may be based on characteristics or attributes from an optical image of the particular potential defect. The potential defect may then be identified as being a systematic defect or not being a systematic defect based on an aggregate or other such combination of the defect scores. For example, if the aggregated defect scores satisfy a threshold condition or value, then the potential defect may be a systematic defect (as are the other potential defects with the same or similar pattern). Otherwise, the potential effect may not be a systematic defect and instead may be a random defect (e.g., a defect that is not a result of a flaw in the design being implemented at the semiconductor wafer).

Advantages of the present disclosure include, but are not limited to, detecting systematic defects earlier in the fabrication process by focusing on the selection of systematic defects to be provided to a review tool. For example, defects resulting from flaws in a new design or process being implemented by the semiconductor fabrication process may be identified earlier so that the design or process may be changed to address the flaws causing the systematic defects. Thus, an improved yield in the semiconductor fabrication process of such semiconductor wafers may be achieved earlier by addressing the root cause of the systematic defects.

FIG. 1 illustrates an example environment of a guided inspection system 100. In general, the guided inspection system 100 may include an inspection tool 110, a systematic defect sampling component 120, and a defect review tool 130.

As shown in FIG. 1, the guided inspection system 100 includes an inspection tool 110 that may be used to provide information from an examination of an object (e.g., a sample from a semiconductor wafer) for defects as a part of a semiconductor fabrication process. The examination can be part of the semiconductor fabrication process and may be carried out during the fabrication of the object. The guided inspection system 100 may further automatically determine semiconductor defect-related information using images obtained during or after wafer fabrication. For example, the inspection tool 110 may receive inputs 105 and may generate a map of potential or candidate defects (e.g., candidate samples) at the semiconductor wafer. The inputs 105 may include, but are not limited to, an image of a semiconductor wafer, design data (e.g., computer aided design (CAD) data that specifies structures or patterns of a design that includes objects), or regions of interest information that specifies particular portions of the semiconductor wafer that have been identified by a user. In some embodiments, the inspection tool 110 may be configured to capture inspection images. For example, the inspection tool 110 may utilize a high-speed and/or low resolution optical system to obtain an image of a semiconductor wafer. The resulting image may be informative of potential defects.

The inspection data 115 from the inspection tool 110 may be provided to a systematic defect sampling component 120. The inspection data 115 may identify locations of potential defects at the semiconductor wafer. In some embodiments, the systematic defect sampling component 120 may be part of a defect detection system. The defect detection system may be configured to process the received inspection data 115 to select candidate samples (e.g., potential defects) for review. For example, the systematic defect sampling component 120 may select one or more of the potential defects or samples from the inspection data 115 to the defect review tool 130 to determine whether the potential defects are actual defects or are not actual defects (e.g., false alarms) and may classify any actual defects. The defect review tool 130 may be configured to capture review images of at least part or a subset of the potential defects detected by inspection tool 110 and selected by the systematic defect sampling component 120. For example, the defect review tool 130 may include a low-speed and/or high-resolution optical system relative to the high-speed and/or low-resolution optical system of the inspection tool 110. In some embodiments, the defect review tool 130 may be a scanning electron microscope (SEM). The output 135 of the defect review tool 130 may then be provided to the systematic defect sampling component 120 to select additional potential defects to be reviewed by the defect review tool 130. For example, the systematic defect sampling component 120 may identify a potential defect that is a systematic defect and may provide the systematic defect to be reviewed by the defect review tool 130.

In operation, the inspection tool 110 may identify locations of potential defects at the semiconductor wafer. The inspection tool 110 may provide the locations of the potential defects to the systematic defect sampling component 120. Subsequently, the systematic defect sampling component 120 may perform an iterative selection process for subsets of the potential defects that have been identified by the inspection tool 110. For example, a first subset of the potential defects may be selected and provided to the defect review tool 130 for classification of the potential defects from the first subset. Defect information from these particular potential defects may then be received. Subsequently, this defect information may be used to identify potential defects for a second subset of the potential defects that are to be reviewed by the systematic defect review tool 130. The potential defects selected for the second subset may be identified as not being similar to other potential defects that have been previously reviewed. Furthermore, the first and second subsets of potential defects may include potential effects that have been identified as being systematic defects. For example, a first subset of the potential defects may be provided to the defect review tool 130. The first subset of the potential defects may be the potential defects that are most likely to be systematic defects (e.g., as based on the calculated score described below). The second subset of the potential defects may then be selected based on the results of the defect review tool 130 with respect to the first subset of the potential defects and the second subset of the potential defects may be the next most likely to be systematic defects after the first subset.

In some embodiments, the inspection tool 110, systematic defect sampling component 120, and defect review tool 130 may be different tools located at the same or at different locations, or a single tool operated in different modes. In the latter case, the tool may be first operated with lower resolution and high speed to obtain images of all or at least a large part of the relevant areas of the object (e.g., corresponding to the inspection image of the inspection tool 110). Once potential defects are detected, the tool can be operated at a higher resolution and possibly lower speed for examining specific locations associated with the potential defects (e.g., corresponding to the operations of the defect review tool 130). In some embodiments, the functionality described herein may be implemented in a defect review tool. For example, the defect review tool may perform operations corresponding to the systematic defect sampling component 120 for selecting potential defects or other such systematic defects that are to be reviewed in particular iterations by the defect review tool. In some embodiments, the systematic defect sampling component 120 may be implemented in a standalone tool or server. For example, the defect inspection system may be implemented in a distributed environment where the inspection review tool, systematic defect sampling component, and the defect review tool are coupled to each other via networks.

Figure 2:
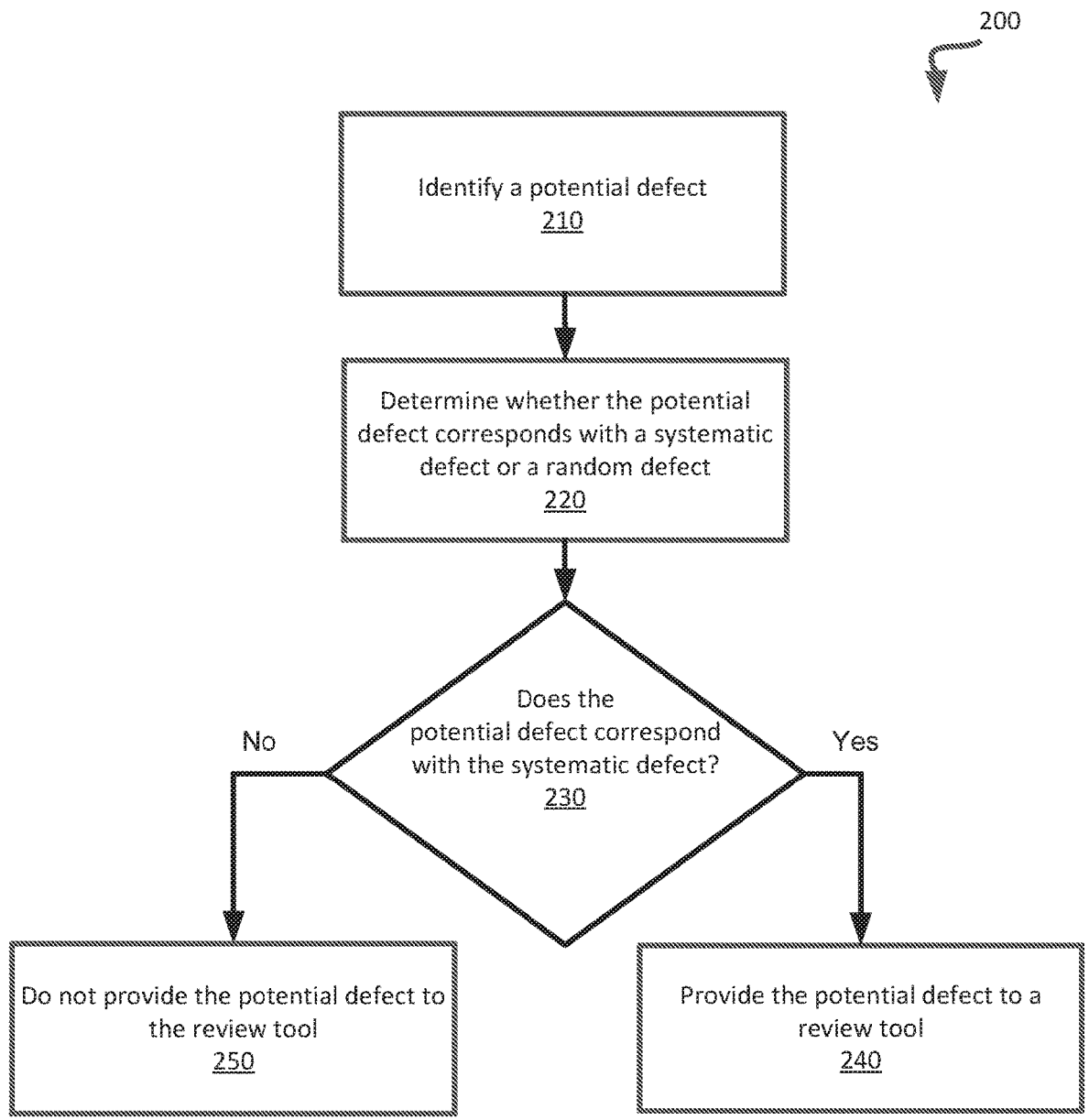
FIG. 2 is a flow diagram of an example method to select a potential defect for review by a review tool based on the potential defect being a systematic defect in accordance with some embodiments.

FIG. 2 is a flow diagram of an example method 200 to select a potential defect for review by a review tool based on the potential defect being a systematic defect. The method 200 may be performed by processing logic that may include hardware (e.g., processing device, circuitry, dedicated logic, programmable logic, microcode, hardware of a device, integrated circuit, etc.), software (e.g., instructions run or executed on a processing device), or a combination thereof. In some embodiments, the method 200 may be performed by the systematic defect sampling component 120 of FIG. 1.

As shown in FIG. 2, the method 200 may begin, at block 210, with processing logic identifying a potential defect. For example, an inspection tool may identify potential or candidate defects at a semiconductor wafer. In some embodiments, the potential or candidate defects may be identified from input data received and analyzed by the inspection tool. For example, the inspection tool may receive or generate an image of the semiconductor wafer and may identify the potential defect from the image. The potential defect may be identified or marked on a map of the semiconductor wafer where the map indicates the locations of potential defects at positions along the semiconductor wafer. The processing logic may subsequently determine whether the potential defect corresponds with a systematic defect or a random defect (block 220). A systematic defect may be a defect from the semiconductor fabrication process that is caused by a pattern or a structure of a design implemented at the semiconductor wafer subjected to the semiconductor fabrication process. A systematic defect may be present at multiple locations at the semiconductor wafer that include or are approximate to the same or similar pattern or structure. A random defect may be a defect that is not caused by the pattern or the structure of a design. For example, a random defect may be a defect that is at one location with a pattern but is not present at other location of the semiconductor wafer that are at or approximate to the same or similar pattern. The random defect may be caused by another flaw during the semiconductor fabrication process that does not result from a design of the semiconductor wafer (e.g., a foreign particle inadvertently landed on the semiconductor wafer during the semiconductor fabrication process). The potential defect may be identified as the systematic defect when a pattern of the potential defect is at multiple locations of the semiconductor wafer and an aggregate defect score for the pattern satisfies a threshold condition. Otherwise, the potential defect may be identified as the random defect when a pattern of the potential defect is not at multiple locations of the semiconductor wafer and/or an aggregate defect score for the pattern does not satisfy the threshold condition. Further details with regards to the identifying of the potential defect as a systematic defect are described in conjunction with FIG. 4.

Referring to FIG. 2, the processing logic may identify whether the potential defect corresponds with the systematic defect (block 230) and may provide the potential defect to a review tool in response to identifying that the potential defect is a systematic defect (block 240). For example, the potential defect may be provided for classification to a defect review tool. In some embodiments, the defect review tool may be used to determine whether the potential effect is an actual defect and/or determine a type of actual defect. The results of the defect review tool may then be used to select subsequent potential defects to be classified or review by the defect review tool. For example, the other potential defects that have or are approximate to the same pattern as the potential effect that was identified as being an actual defect may also be provided to the defect review tool. Otherwise, if the processing logic identifies that the potential defect does not correspond with the systematic defect, then the processing logic may not provide the potential defect to the review tool (block 250). For example, the potential defect may be identified as the random defect and may not be provided to the defect review tool. In some embodiments, another potential defect may then be identified and this new potential defect may be analyzed to determine whether it is a systematic defect.

Figure 3A:
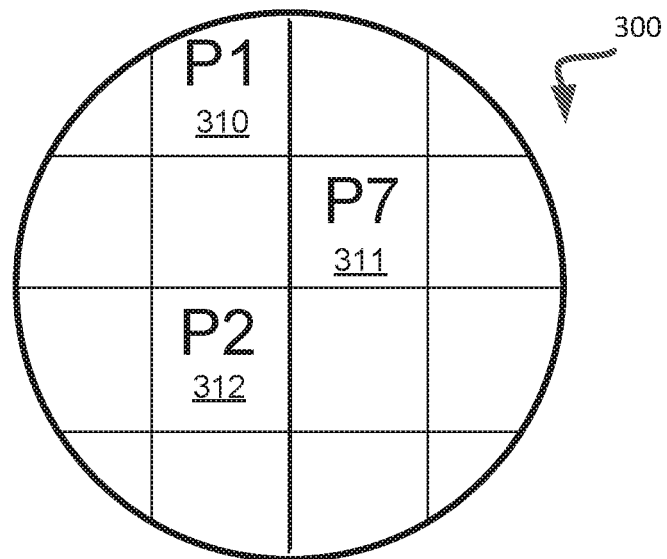
FIG. 3A illustrates a semiconductor wafer that does not include systematic defects in accordance with some embodiments.

FIG. 3A illustrates a semiconductor wafer 300 that does not include systematic defects. The potential defects of the semiconductor wafer 300 may be identified by the systematic defect sampling component 120 of FIG. 1.

As shown in FIG. 3A, the semiconductor wafer 300 may correspond to a map of locations of the semiconductor wafer with potential defects. The potential defects may correspond to a particular pattern of a design of a circuit or structure at the semiconductor wafer. For example, the pattern may represent structures or portions of the structures (e.g., electrical contacts, vias, interconnect wires, dielectric structures, etc.) of the design that are formed during the semiconductor fabrication process. A first potential defect 310, a second potential defect 311, and a third potential defect 312 of the semiconductor wafer 300 may be identified. Furthermore, the first potential defect 310 may correspond to a first pattern, the second potential defect may correspond to a second pattern, and the third potential effect 312 may correspond to a third pattern where each of the first, second, and third patterns are different or not part of the same type of structure. As a result, the first potential defect 310, second potential defect 311, and the third potential defect 312 may not be considered systematic defects since these potential effects do not share the same or similar pattern with another potential defect.

Figure 3B:
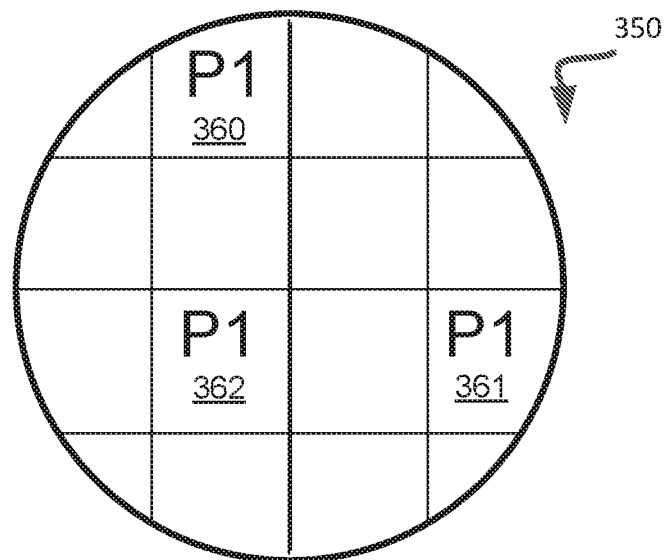
FIG. 3B illustrates a semiconductor wafer that includes systematic defects in accordance with some embodiments.

FIG. 3B illustrates a semiconductor wafer 350 that includes systematic defects. The systematic defects of the semiconductor wafer 350 may be identified by the systematic defect sampling component 120 of FIG. 1.

As shown in FIG. 3B, the map of locations of the semiconductor wafer with potential defects may include a first potential defect 360, a second potential defect 361, and a third potential defect 362. Each of the first potential defect 360, the second potential defect 361, and the third potential defect 362 may correspond to the same pattern 'P 1.' For example, each of these potential defects may be at or approximate to a same or similar pattern. As a result, the first potential defect 360, second potential defect 361, and the third potential defect 362 may be considered systematic defects since these potential effects share the same or similar pattern. In some embodiments, the first potential defect 360, second potential defect 361, and the third potential defect 362 may each be assigned a defect score that represents a probability of each corresponding defect being an actual defect based on a characteristic of an image of the corresponding defect. The first potential defect 360, second potential defect 361, and the third potential defect 362 may be considered systematic defects based on these defects having the same pattern and an aggregate defect score satisfying a threshold value or condition as described in further detail below.

Although FIG. 3B shows the semiconductor wafer 350 as having three potential defects, the semiconductor wafer 350 may include any number of potential defects and/or a distribution of potential defects that may be random defects and potential defects that may be systematic defects. In some embodiments, different groups of systematic defects may be identified. For example, a first group of potential defects sharing a first pattern may be identified and a second group of potential defects sharing a second pattern that is different than the first pattern may be identified. A potential defect from the first group may be determined to be a systematic defect and may be provided to a defect review tool as previously described. Similarly, a second potential defect from the second group may also be determined to be a systematic defect and may be provided to the defect review tool separately from the first group of potential defects.

Figure 4:
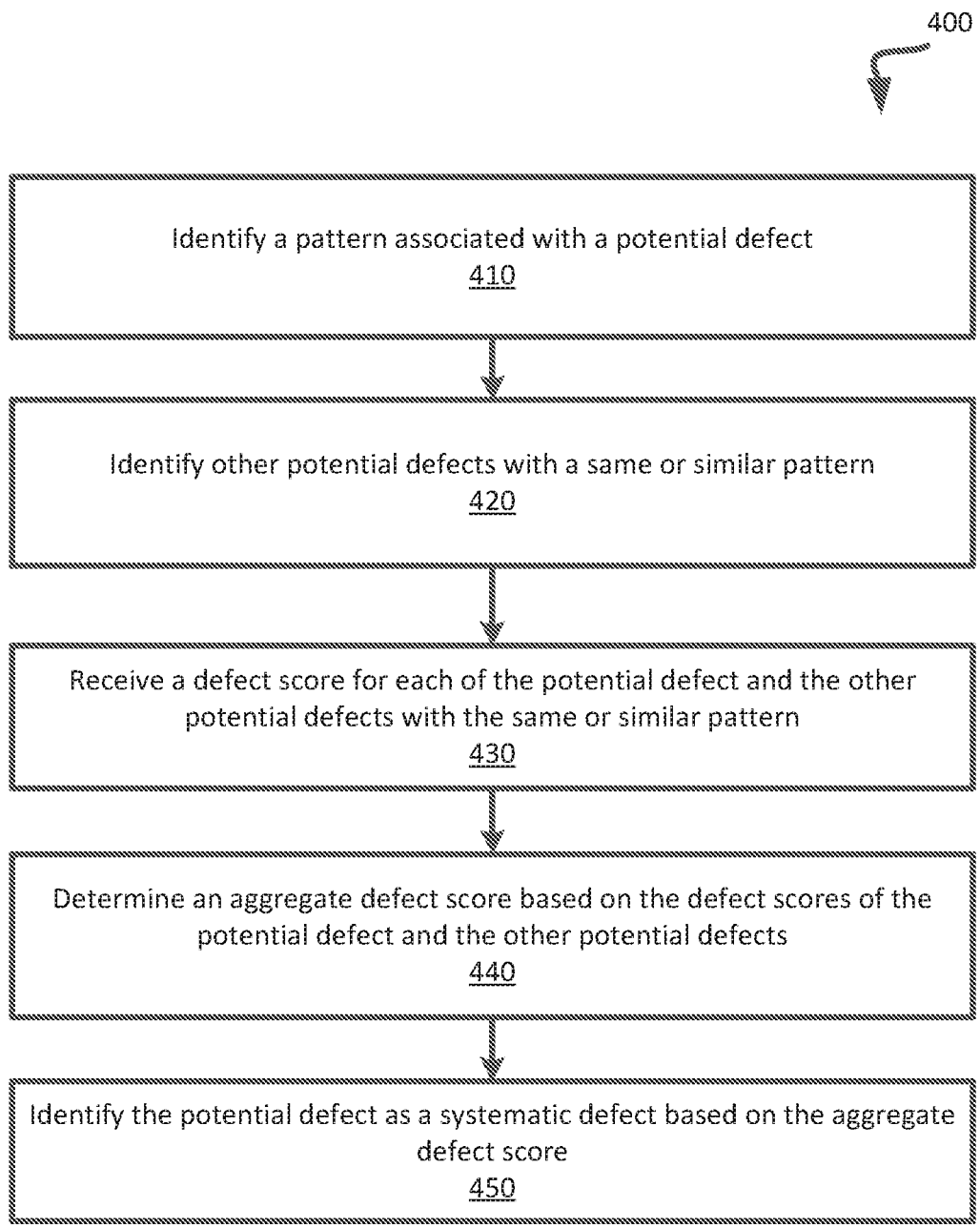
FIG. 4 is a flow diagram of an example method to identify whether a potential defect is a systematic defect or a random defect in accordance with some embodiments of the present disclosure.

FIG. 4 is a flow diagram of an example method 400 to identify whether a potential defect is a systematic defect or a random defect. The method 400 may be performed by processing logic that may include hardware (e.g., processing device, circuitry, dedicated logic, programmable logic, microcode, hardware of a device, integrated circuit, etc.), software (e.g., instructions run or executed on a processing device), or a combination thereof. In some embodiments, the method 400 may be performed by the systematic defect sampling component 120 of FIG. 1.

As shown in FIG. 4, the method 400 may begin, at block 410, with the processing logic identifying a pattern associated with a potential defect. For example, a pattern of a structure that is at a location of the potential defect or is approximate (e.g., within a threshold distance) to the location of the potential defect may be identified. The pattern associated with the potential defect may be identified from computer aided design (CAD) information that specifies design characteristics of the semiconductor wafer. In some embodiments, the potential defect may be identified based on optical characteristics of the potential defect from an optical image of the semiconductor wafer. The optical image of the semiconductor wafer may be correlated with or mapped to the CAD information of the semiconductor wafer to identify which particular structures or patterns are at particular locations of the semiconductor wafer. The processing logic may further identify other potential defects with a same or similar pattern (block 420). For example, other potential defects may be identified from the optical image and corresponding structures or patterns at the locations of the other potential defects may be identified from the CAD information. The same or similar pattern may correspond to an identical pattern or a pattern that is part of the same structure or a pattern that is a part of a structure where the design of the structure is repeated at various locations of the semiconductor wafer. The processing logic may further receive a defect score for each of the potential defect and the other potential defects with the same or similar pattern (block 430). The defect score may be based on a probability of a potential defect being an actual defect. Such a probability may be based on characteristics of the potential defect. For example, the defect score may be based on optical characteristics of the potential defect and/or design characteristics of the pattern associated with the potential defect. Such characteristics may correspond to a noise signature of the potential defect in the optical space. In some embodiments, the noise signature may be based on various characteristics such as a size, dimensions, gray color level, or other such attribute of the potential defect. The processing logic may further determine an aggregate defect score based on the defect scores of the potential defect and the other potential defects (block 440). For example, a combination of the defect scores may be used to determine the aggregate defect score. In some embodiments, the aggregate defect score may be an average of the defect scores of the potential effect and the other potential effects. In the same or alternative embodiments, the aggregate defect score may be based on a number of the potential defects with the same or similar pattern and the respective defect scores. For example, if more potential defects are associated with the same or similar pattern, then the aggregate defect score may be higher than when fewer potential defects are associated with the same or similar pattern.

Referring to FIG. 4, the processing logic may identify the potential defect as a systematic defect based on the aggregate defect score (block 450). For example, if the aggregate defect score equals or exceeds a threshold value or threshold condition, then the potential defect may be considered a systematic defect. Similarly, the other potential defects with the same or similar pattern may also be considered systematic defects. Otherwise, if the aggregate defect score does not equal or exceed the threshold value or threshold condition, then the potential defect may be considered a random defect.

In some embodiments, similar patterns from the design data (e.g., CAD information) may be identified and potential defects that are at or approximate to the similar patterns may be identified. The aggregate defect score may then be determined for the similar patterns. Furthermore, in some embodiments, the potential defects may be identified based on known hotspots of the design, particular regions of interest (e.g., portions of the design), or other such information.

Figure 5:
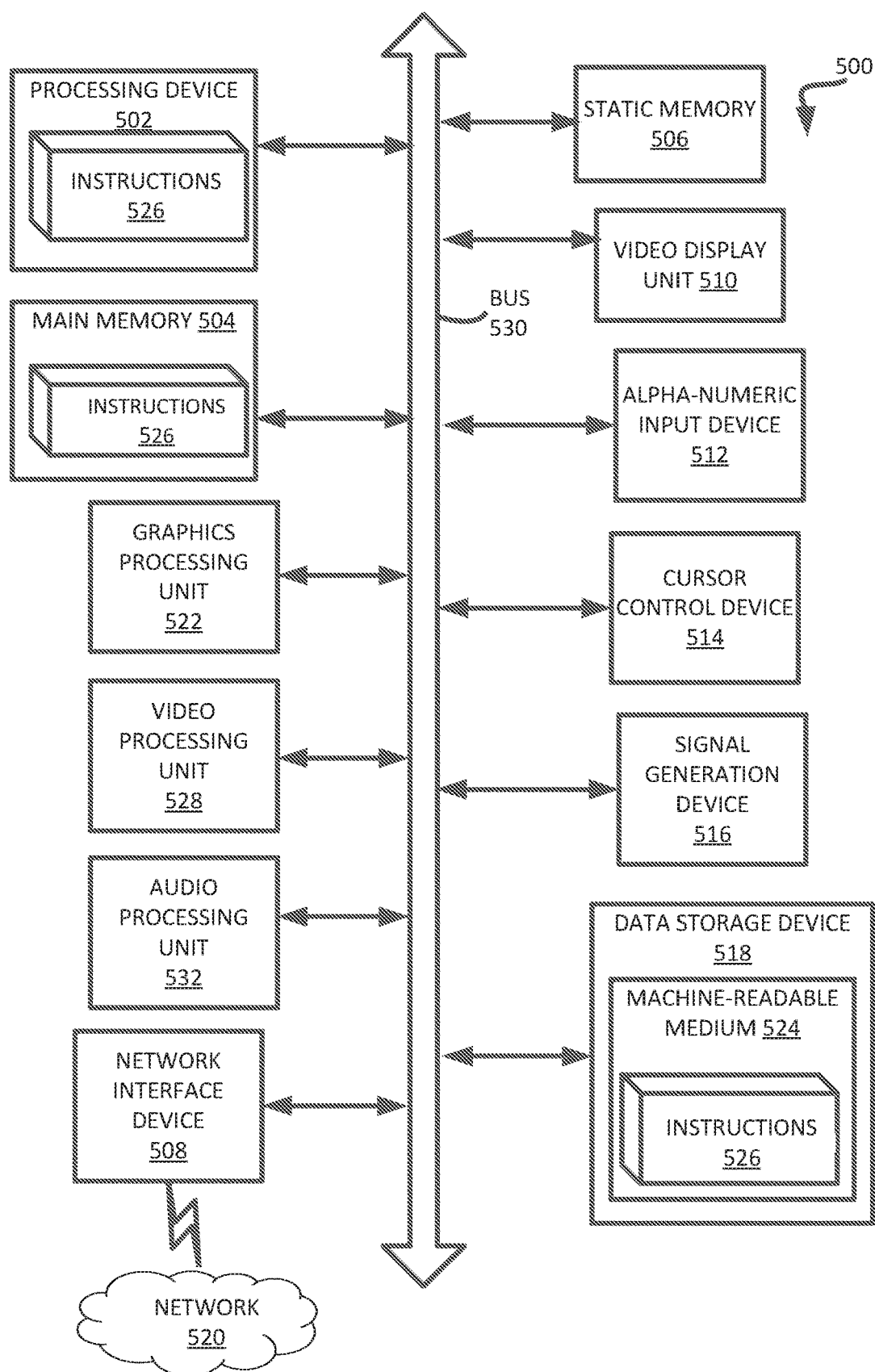
FIG. 5 is a block diagram of an example computer system in which implementations of the present disclosure may operate.

FIG. 5 illustrates an example machine of a computer system 500 within which a set of instructions, for causing the machine to perform any one or more of the methodologies discussed herein, may be executed. In alternative implementations, the machine may be connected (e.g., networked) to other machines in a LAN, an intranet, an extranet, and/or the Internet. The machine may operate in the capacity of a server or a client machine in client-server network environment, as a peer machine in a peer-to-peer (or distributed) network environment, or as a server or a client machine in a cloud computing infrastructure or environment.

The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 500 includes a processing device 502, a main memory 804 (e.g., read-only memory (ROM), flash memory, dynamic random access memory (DRAM) such as synchronous DRAM (SDRAM) or Rambus DRAM (RDRAM), etc.), a static memory 506 (e.g., flash memory, static random access memory (SRAM), etc.), and a data storage device 518, which communicate with each other via a bus 530.

Processing device 502 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 502 may also be one or more special-purpose processing devices such as an application specific integrated circuit (ASIC), a field programmable gate array (FPGA), a digital signal processor (DSP), network processor, or the like. The processing device 502 is configured to execute instructions 526 for performing the operations and steps discussed herein.

The computer system 500 may further include a network interface device 508 to communicate over the network 520. The computer system 500 also may include a video display unit 510 (e.g., a liquid crystal display (LCD) or a cathode ray tube (CRT)), an alphanumeric input device 512 (e.g., a keyboard), a cursor control device 514 (e.g., a mouse), a graphics processing unit 522, a signal generation device 516 (e.g., a speaker), graphics processing unit 522, video processing unit 528, and audio processing unit 532.

The data storage device 518 may include a machine-readable storage medium 524 (also known as a computer-readable medium) on which is stored one or more sets of instructions or software 526 embodying any one or more of the methodologies or functions described herein. The instructions 526 may also reside, completely or at least partially, within the main memory 504 and/or within the processing device 502 during execution thereof by the computer system 500, the main memory 504 and the processing device 502 also constituting machine-readable storage media.

In one implementation, the instructions 526 include instructions to implement functionality corresponding to a systematic defect sampling component (e.g., systematic defect sampling component 120 of FIG. 1). While the machine-readable storage medium 524 is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "determining" or "executing" or "performing" or "collecting" or "creating" or "sending" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The algorithms and displays presented herein are not inherently related to any particular computer or other apparatus. Various general purpose systems may be used with programs in accordance with the teachings herein, or it may prove convenient to construct a more specialized apparatus to perform the method. The structure for a variety of these systems will appear as set forth in the description below. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

In the foregoing specification, implementations of the disclosure have been described with reference to specific example implementations thereof. It will be evident that various modifications may be made thereto without departing from the broader spirit and scope of implementations of the disclosure as set forth in the following claims. The specification and drawings are, accordingly, to be regarded in an illustrative sense rather than a restrictive sense.

What is claimed is:

1. A system comprising:
  a memory; and
  a processor, operatively coupled with the memory, to:
    identify a candidate defect at a semiconductor wafer;
    determine whether the candidate defect at the semiconductor wafer corresponds to a systematic defect or a random defect by:
      identifying a pattern associated with the candidate defect;
      identifying other candidate defects at the semiconductor wafer that are associated with a same pattern; and
      generating a combined defect probability score for the candidate defect based on a defect probability score of the candidate defect and other defect probability scores of the other candidate defects that are associated with the same pattern; and
    in response to determining that the candidate defect at the semiconductor wafer corresponds to the systematic defect, provide the candidate defect at the semiconductor wafer to a defect review tool for review by the defect review tool.

2. The system of claim 1, wherein the pattern associated with the candidate defect corresponds to a structure of the semiconductor wafer that is at or approximate to the candidate defect, and wherein the other candidate defects that are associated with the same pattern correspond to candidate defects that are at or approximate another structure of the semiconductor wafer with the same pattern.

3. The system of claim 1, wherein the processor is further to:
  determine that the candidate defect is the systematic defect responsive to the combined defect probability score for the candidate defect satisfying a threshold value; and
  determining that the candidate defect is the random defect responsive to the combined defect probability score for the candidate defect not satisfying the threshold value.

4. The system of claim 1, wherein the combined defect probability score is higher when a number of the other candidate defects that are associated with the same pattern as the candidate defect is larger than when a number of the other candidate defects that are associated with the same pattern as the candidate defect is smaller.

5. The system of claim 1, wherein the candidate defect is identified based on an optical image of the semiconductor wafer and wherein the candidate defect is determined to correspond to a systematic defect or a random defect based on design data of the semiconductor wafer.

6. The system of claim 1, wherein the processor is further to:
  in response to determining that the candidate defect at the semiconductor wafer corresponds to the random defect, determine to not provide the candidate defect at the semiconductor wafer to the defect review tool for review by the defect review tool.

7. A method comprising:
  identifying a candidate defect at a semiconductor wafer;
  determining, by a processor, whether the candidate defect at the semiconductor wafer corresponds to a systematic defect or a random defect by:
    identifying a pattern associated with the candidate defect;
    identifying other candidate defects at the semiconductor wafer that are associated with a same pattern; and
    generating a combined defect probability score for the candidate defect based on a defect probability score of the candidate defect and other defect probability scores of the other candidate defects that are associated with the same pattern; and
  in response to determining that the candidate defect at the semiconductor wafer corresponds to the systematic defect, providing the candidate defect at the semiconductor wafer to a defect review tool for review by the defect review tool.

8. The method of claim 7, wherein the pattern associated with the candidate defect corresponds to a structure of the semiconductor wafer that is at or approximate to the candidate defect, and wherein the other candidate defects that are associated with the same pattern correspond to candidate defects that are at or approximate another structure of the semiconductor wafer with the same pattern.

9. The method of claim 7, further comprising:
  determining that the candidate defect is the systematic defect responsive to the combined defect probability score for the candidate defect satisfying a threshold value; and
  determining that the candidate defect is the random defect when repsonsive to the combined defect probability score for the candidate defect not satisfying the threshold value.

10. The method of claim 7, wherein the combined defect probability score is higher when a number of the other candidate defects that are associated with the same pattern as the candidate defect is larger than when a number of the other candidate defects that are associated with the same pattern as the candidate defect is smaller.

11. The method of claim 7, wherein the candidate defect is identified based on an optical image of the semiconductor wafer and wherein the candidate defect is determined to correspond to a systematic defect or a random defect based on design data of the semiconductor wafer.

12. The method of claim 7, further comprising:
in response to determining that the candidate defect at the semiconductor wafer corresponds to the random defect, determining to not provide the candidate defect at the semiconductor wafer to the defect review tool for review by the defect review tool.

13. A non-transitory computer readable medium comprising instructions, which when executed by a processor, cause the processor to perform operations comprising:
identifying a candidate defect at a semiconductor wafer;
determining, by the processor, whether the candidate defect at the semiconductor wafer corresponds to a systematic defect or a random defect by:
identifying a pattern associated with the candidate defect;
identifying other candidate defects at the semiconductor wafer that are associated with a same pattern; and
generating a combined defect probability score for the candidate defect based on a defect probability score of the candidate defect and other defect probability scores of the other candidate defects that are associated with the same pattern; and
in response to determining that the candidate defect at the semiconductor wafer corresponds to the systematic defect, provide the candidate defect at the semiconductor wafer to a defect review tool for review by the defect review tool.

14. The non-transitory computer readable medium of claim 13, wherein the pattern associated with the candidate defect corresponds to a structure of the semiconductor wafer that is at or approximate to the candidate defect, and wherein the other candidate defects that are associated with the same pattern correspond to candidate defects that are at or approximate another structure of the semiconductor wafer with the same pattern.

15. The non-transitory computer readable medium of claim 13, the operations further comprising:
determine that the candidate defect is the systematic defect when repsonsive to the combined defect probability score for the candidate defect satifies satisfying a threshold value; and
determining that the candidate defect is the random defect when responsive to the combined defect probability score for the candidate defect does not satisfying the threshold value.

16. The non-transitory computer readable medium of claim 13, wherein the combined defect probability score is higher when a number of the other candidate defects that are associated with the same pattern as the candidate defect is larger than when a number of the other candidate defects that are associated with the same pattern as the candidate defect is smaller.

17. The non-transitory computer readable medium of claim 13, wherein the candidate defect is identified based on an optical image of the semiconductor wafer and wherein the candidate defect is determined to correspond to a systematic defect or a random defect based on design data of the semiconductor wafer.

* * * * *

UNITED STATES PATENT AND TRADEMARK OFFICE
CERTIFICATE OF CORRECTION

Page 1 of 1

PATENT NO. : 10,605,745 B2
APPLICATION NO. : 16/022566
DATED : March 31, 2020
INVENTOR(S) : Yotam Sofer et al.

It is certified that error appears in the above-identified patent and that said Letters Patent is hereby corrected as shown below:

In the Claims

In Claim 9, Column 12, Line 61, delete "when repsonsive" and insert --responsive--

In Claim 15, Column 14, Line 12, delete "when repsonsive" and insert --responsive--

In Claim 15, Column 14, Line 13, delete "satifies"

In Claim 15, Column 14, Line 16, delete "when"

In Claim 15, Column 14, Line 17, delete "does"

Signed and Sealed this
Ninth Day of June, 2020

Andrei Iancu
*Director of the United States Patent and Trademark Office*